United States Patent [19]

Lang

[11] Patent Number: 4,892,962
[45] Date of Patent: Jan. 9, 1990

[54] PROCESS FOR THE PREPARATION OF 2,2-DIFLUOROPENT-4-ENOIC ACIDS AND ACID DERIVATIVES

[75] Inventor: Robert W. Lang, Pratteln, Switzerland

[73] Assignee: Ciba-Geigy Corporation, Ardsley, N.Y.

[21] Appl. No.: 129,198

[22] Filed: Dec. 7, 1987

[30] Foreign Application Priority Data

Dec. 18, 1986 [CH] Switzerland ............ 5058/86

[51] Int. Cl.$^4$ ............................................. C07F 7/10
[52] U.S. Cl. ......................................... 556/416; 556/427; 556/442
[58] Field of Search ................. 556/442, 416, 427

[56] References Cited

PUBLICATIONS

M. Kolb et al., Tetrahedron Letters, 27, 4437 (1986).
Chem. Abstract Index Guide A 133.

*Primary Examiner*—John Doll
*Assistant Examiner*—Stuart L. Hendrickson
*Attorney, Agent, or Firm*—Stephen V. O'Brien

[57] ABSTRACT

The reaction of allyl bromo- or chloro-difluoroacetates with monochlorisilanes in the presence of zinc with heating gives silyl esters of $\alpha,\alpha$-difluoro-$\gamma,\delta$-pentenoic acids. The free acids, from which acid derivatives can be prepared by conventional methods, are obtained by hydrolysis. The pentenoic acids and pentenoic acid derivatives are suitable for the preparation of polymers and copolymers, from which metal-organic polymers and copolymers having catalytic properties are obtainable.

6 Claims, No Drawings

PROCESS FOR THE PREPARATION OF 2,2-DIFLUOROPENT-4-ENOIC ACIDS AND ACID DERIVATIVES

The invention relates to a process for the preparation of 2,2-difluoropent-4-enoic acids and acid derivatives by rearrangement of allyl bromo- or chloro-difluoro acetates in the presence of zinc and monochlorosilanes, and to substituted 2,2-difluoropent-4-enoic acids and acid derivatives and allyl chlorodifluoroacetates.

In Bulletin de la Société Chimique de France, No. 9–10, page 2077 (1974), J. F. Normant et al. described the preparation of 2,2-difluoropent-4-en-1-oic acid by the reaction of allyl alcohol with tetrafluoroethylene, followed by a treatment with lithium butyl and subsequent hydrolysis. This laboratory method is unsuitable for a process on an industrial scale.

In addition to 2,2-difluoropent-4-en-1-oic acid, its acid chloride and acid anhydride are also described in Tetr. Lett., volume 27, No. 37, pages 4437–4440 (1986).

The present invention relates to a process for the preparation of compounds of the formula I

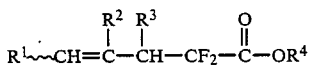
(I)

in which $\sim\sim\sim$ signifies cis/trans isomers, $R^1$ is H, $C_1$–$C_{24}$-alkyl or $C_6$–$C_{12}$-aryl, $C_7$–$C_{16}$-aralkyl or $C_8$–$C_{40}$-alkaralkyl which are unsubstituted or substituted in the aryl group of $C_1$–$C_6$-alkoxy, $C_1$–$C_6$-alkylthio, F, Cl, Br or —CN, $R^2$ and $R^3$ independently of one another are H or $C_1$–$C_{24}$-alkyl, or $R^1$ and $R^3$ together are unsubstituted or $C_1$–$C_6$-alkyl-substituted $C_1$–$C_5$-alkylene or $C_2$–$C_5$-alkenylene, $R^2$ and $R^3$ together or $R^1$ and $R^2$ together are unsubstituted or $C_1$–$C_6$-alkyl-substituted $C_1$–$C_6$-alkylene or $C_3$–$C_6$-alkenylene, and $R^4$ is —$SiR^5R^6R^7$, in which $R^5$, $R^6$ and $R^7$ independently of one another are $C_1$–$C_{12}$-alkyl, phenyl or benzyl, and the acids and acid derivatives thereof, which process comprises heating 1 mol of an allyl monobromo- or monochloro-difluoroacetate of the formula II

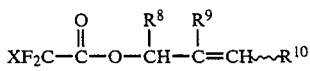
(II)

in which $\sim\sim\sim$ is as defined above, X is Cl or Br, $R^8$ is as defined for $R^1$, $R^9$ is as defined for $R^2$, $R^{10}$ is as defined for $R^3$, $R^8$ and $R^9$ are as defined for $R^1$ and $R^2$, $R^8$ and $R^{10}$ are as defined for $R^1$ and $R^3$, and $R^9$ and $R^{10}$ are as defined for $R^2$ and $R^3$, in the presence of at least 1 mol of zinc and of at least 1 mol of a monochlorosilane $R^5R^6R^7SiCl$, in which $R^5$, $R^6$ and $R^7$ are as defined above, isolating the compounds of the formula I or hydrolysing them to prepare the acids and, if appropriate, preparing acid derivatives from the acids.

X is preferably Cl.

Alkyl $R^1$ can be branched and especially linear alkyl having 1 to 24, preferably 1 to 20 and especially 1 to 12 C atoms. Examples are: methyl, ethyl, n- and i-propyl, n-, i- and t-butyl, 2-methylbut-4-yl, n-pentyl, 3-methylpent-1-yl, pent-2-yl, pent-3-yl, n-hexyl, hex-2-yl, hex-3-yl, n-heptyl, hept-2-yl, hept-3-yl, 2-ethylhex-1-yl, n-octyl, oct-2-yl, oct-3-yl, oct-4-yl, nonyl, decyl, undecyl, dodecyl, tridecyl, tetradecyl, pentadecyl, hexadecyl, heptadecyl, octadecyl, nonadecyl and eicosyl.

Aryl, aralkyl or alkaralkyl $R^1$ can be monosubstituted to trisubstituted, preferably monosubstituted or disubstituted, by $C_1$–$C_6$- or preferably $C_1$–$C_4$-alkoxy groups or -alkylthio groups or F, Cl, Br or —CN. Examples of alkoxy and alkylthio are methoxy, ethoxy, n- and i-propoxy, n-, i- and t-butoxy, pentoxy, hexoxy, methylthio, ethylthio, propylthio and butylthio.

Aryl $R^1$ preferably contains 6 to 10 C atoms and is especially phenyl or naphthyl. Aralkyl $R^1$ preferably contains 7 to 12 C atoms and is preferably phenylalkyl having 1 to 3 C atoms in the alkylene group. Alkaralkyl $R^1$ preferably contains 8 to 34 C atoms and preferably is alkylphenylalkyl which in particular contains 1 to 12 C atoms in the alkyl group and 1 to 3 C atoms in the alkylene group. Examples are: phenyl, benzyl, 1-phenyleth-2-yl, 1-phenylprop-1-yl, methylphenyl, dimethylphenyl, ethylphenyl, ethylmethylphenyl, propylphenyl, butylphenyl, hexylphenyl, decylphenyl, methylbenzyl, dimethylbenzyl, ethylbenzyl, propylbenzyl, butylbenzyl, octylbenzyl, dodecylbenzyl, 1-(methylphenyl)eth-1-yl, 1-(dimethylphenyl)-prop-1-yl and 1-(octylphenyl)eth-1-yl.

$R^2$ and $R^3$ can independently of one another be branched and preferably linear $C_1$–$C_{24}$-alkyl, preferably $C_1$–$C_{12}$-alkyl and especially $C_1$–$C_6$-alkyl. Examples of alkyl have been given above for the group $R^1$. Preferably, $R^2$ and $R^3$ are each H.

Alkylene or alkenylene $R^1$ and $R^3$, $R^1$ and $R^2$ or $R^2$ and $R^3$ together can be monosubstituted to trisubstituted, preferably monosubstituted or disubstituted by alkyl groups having 1 to 6 and preferably 1 to 4 C atoms. Examples are: methyl, ethyl, n- and i-propyl, n-, i- and t-butyl, pentyl and hexyl.

Alkylene $R^1$ and $R^3$ together preferably contains 1 to 3 C atoms. Alkenylene $R^1$ and $R^3$ together preferably contains 2 to 3 C atoms. Alkylene $R^2$ and $R^3$ together and $R^1$ and $R^2$ together preferably contains 1 to 4 C atoms. Alkenylene $R^2$ and $R^3$ together preferably contain 3 or 4 C atoms. Alkenylene $R^1$ and $R^2$ together preferably contains 3 or 4 C atoms. Examples of alkylene or methylene, ethylene, n-propylene, n-butylene, n-pentylene and n-hexylene. Examples of alkenylene are ethenylene, n-propenylene, n-but-1-enylene, n-but-2-enylene, n-pentenylene and n-hexenylene.

In the compounds of the formula I, $R^4$ is an $R^5,R^6R^7Si$ group, in which alkyl $R^5$, $R^6$ and $R^7$ is preferably linear or branched $C_1$–$C_8$-alkyl, in particular $C_1$–$C_6$-alkyl and especially $C_1$–$C_4$-alkyl. Particularly preferably, $R^5$, $R^6$ and $R^7$ are identical or different alkyl radicals having especially 1 to 8 C atoms.

Examples of $R^5$, $R^6$ and $R^7$ are: methyl, ethyl, n-propyl, i-propyl, n-, i- or t-butyl, pent-1-yl, 1-, 2- or 3-hexyl, 1,2,2-trimethyleth-1-yl, 1,1,2,2-tetramethyleth-1-yl (thexyl), heptyl, octyl, decyl, dodecyl, phenyl and benzyl. Preferably, $R^5$, $R^6$ and $R^7$ are methyl.

Examples of the $R^5R^6R^7Si$ group are: methyldiethylsilyl, dimethylpentylsilyl, trimethylsilyl, ethyldipropylsilyl, methylethylpropylsilyl, diethylpropylsilyl, triethylsilyl, dimethylbutylsilyl, n-propyldibutylsilyl, i-propyldiethylsilyl, i-propyldimethylsilyl, tri-n-propylsilyl, tri-n-butylsilyl, n-butyldimethylsilyl, n-butyldiethylsilyl, t-butyldimethylsilyl, tri-n-pentylsilyl, n-pentyldimethylsilyl, (1,2,2-trimethyleth-1-yl)-dimethylsilyl, (1,1,2,2-tetramethylethyl)-dimethylsilyl, tri-n-octylsilyl and n-octyldimethylsilyl.

In a preferred embodiment of the process according to the invention, $R^1$ is H, $C_1$–$C_{20}$-alkyl, or phenyl, $C_7$–$C_{16}$-phenylalkyl or $C_8$–$C_{30}$-alkylphenylalkyl, which are unsubstituted or substituted in the phenyl group by $C_1$-$C_6$-alkoxy, $C_1$-$C_6$-alkylthio, F, Cl, Br or —CN, $R^2$ and $R^3$ independently of one another are H or $C_1$-$C_{12}$-alkyl, $R^1$ and $R^3$ together are $C_1$-$C_3$-alkylene or $C_2$-$C_3$-alkenylene, or $R^2$ and $R^3$ together or $R^1$ and $R^2$ together are $C^1$-$C_4$-alkylene or $C_3$-$C_4$-alkenylene.

In a further preferred embodiment of the process, $R^1$ is H or $C_1$-$C_{20}$-alkyl and $R^2$ and $R^3$ are H or $C_1$-$C_6$-alkyl, especially H.

Acids and acid derivatives can also be prepared by the process according to the invention. In the case of the acids, $R^4$ in the formula I is H. The acid derivatives can be anhydrides, esters, amides, halides or salts of the carboxylic acids of the formula I, in which $R^4$ is H.

A preferred group of acids and acid derivatives are those in which $R^4$ in the formula I is H, $C_1$-$C_{18}$-acyl, the radical of a monohydric alcohol after removal of one hydroxyl group, a metal cation or an ammonium cation, or the group $R^4O—$ is replaced by F, Cl, Br, —NH$_2$ or the radical of a primary or secondary amine after removal of one H atom.

In the case of the anhydrides, the radical $R^4$ is, for example, of the formula

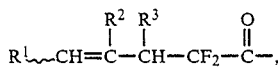

in which, $R^1$, $R^2$ and $R^3$ are as defined above. In the case of mixed anhydrides, $R^4$ is a $C_1$-$C_{18}$-acyl radical, preferably a $C_1$-$C_{12}$-acyl radical. The acyl radical can be of the formula $R^{11}CO—$, in which $R^{11}$ is H or unsubstituted or halogen-substituted, especially F- or Cl-substituted linear or branched $C_1$-$C_{12}$-alkyl, especially $C_1$-$C_6$-alkyl, cyclopentyl, cyclohexyl, phenyl, benzyl or phenylethyl. Examples of $R^{11}$ is methyl, ethyl, n- and i-propyl, n-, i- and t-butyl, pentyl, hexyl, chloromethyl, dichloromethyl, trichloromethyl, fluoromethyl, difluoromethyl, trifluoromethyl, chlorodifluoromethyl and dichlorofluoromethyl.

In the case of the esters, $R^4$ in the formula I is the radical of an alcohol having preferably 1 to 20, in particular 1–12 and especially 1 to 8 C atoms, after removal of one hydroxyl group. $R^4$ can, for example, be linear or branched $C_1$-$C_{20}$-alkyl, in particular $C_1$-$C_{12}$-alkyl and especially $C_1$-$C_6$-alkyl, $C_5$- or $C_6$-cycloalkyl, phenyl, $C_1$-$C_6$-alkylphenyl, phenyl-$C_1$-$C_3$-alkyl or $C_1$-$C_6$-alkylphenyl-$C_1$-$C_3$-alkyl. Examples of such radicals are as given above for $R^1$.

In the case of the amides, the group —OR$^4$ in the formula I is preferably of the formula —NR$^{12}$R$^{13}$, in which $R^{12}$ and $R^{13}$ independently of one another are H, OCH$_3$, $C_1$-$C_{12}$-alkyl, preferably $C_1$-$C_6$-alkyl, cyclopentyl, cyclohexyl, phenyl or benzyl, or $R^{12}$ and $R^{13}$ together are tetramethylene, pentamethylene or 3-oxapentylene. Examples of alkyl have been given above.

In the case of the halides, the group —OR$^4$ in the formula I is preferably F, Br and especially Cl.

In the case of the salts, $R^4$ is, for example, a metal cation or ammonium cation. Preferred metal cations are alkaline earth metal cations and especially alkali metal cations. Preferred ammonium cations are NH$_4$ ± and the cations of primary, secondary and tertiary amines which can be substituted by $C_1$-$C_6$-alkyl, $C_1$-$C_6$-hydroxyalkyl, cyclopentyl, cyclohexyl, phenyl or benzyl, tetramethylene, pentamethylene or 3-oxapentylene.

The process according to the invention is preferably carried out at temperatures from 30° to 150° C., particularly 50° to 120° C. and especially 50° to 100° C., and advantageously in the presence of a inert, polar and aprotic solvent. Examples of suitable solvents are ethers, for example diethyl ether, dibutyl ether, ethylene glycol dimethyl ether, diethylene glycol dimethyl ether, tetrahydrofuran and dioxane, esters, for example methyl acetate, nitriles, for example acetonitrile, sulfones and sulfoxides, for example dimethyl sulfone, tetramethylene sulfone and dimethyl sulfoxide, and halogenated aromatic hydrocarbons, for example chlorobenzene and chlorotoluene.

The reactants are employed in at least molar ratios. It has proved to be advantageous to use Zn in excess of up to 0.1 mol and a chlorosilane in an excess of up to 0.5 mol, relative to the compound of the formula II.

The process can be carried out in such a way that the reactants and, if appropriate, a solvent are introduced into a reaction vessel and then heated until the reaction has ended. The reaction is advantageously initiated, for example, by adding a little iodine. The zinc can be activated beforehand (cf. Fieser and Fieser, Reagents for Organic Synthesis, volume I, John Wiley, N.Y., page 1276 (1967)). The zinc is advantageously employed in the form of zinc dust.

The compounds of the formula I can be isolated in the conventional manner, for example by filtering off the zinc halide which has precipitated, distilling off the solvent used and then further purifying the residue by crystallization, distillation or chromatographic methods, depending on its consistency.

The carboxylic acids of the formula I are advantageously prepared by hydrolysis of the reaction mixture, for example with water, if appropriate after removal of the zinc halide, followed by extraction of the hydrolysis product, which has been rendered basic by means of, for example, NaOH, with a hydrocarbon (pentane, hexane, methylcyclohexane). The aqueous phase is then acidified, for example with hydrochloric acid, and the acid aqueous phase is extracted with a polar aprotic solvent. An example of a suitable solvent is ethyl acetate. The organic phase is dried in the conventional manner, for example with MgSO$_4$, the solvent is removed and the product is further purified, for example by means of distillation.

The acid derivatives of compounds of the formula I are obtained by conventional methods, for example by treatment of the acids with dehydrating agents (for example phosphorus pentoxide) or halogenating agents (for example PCl$_5$) for the preparation of the anhydrides or halides respectively, and by esterification, transesterification, amidation or salt formation for the preparation of the esters, amides and salts.

The invention also relates to the novel compounds of the formula II

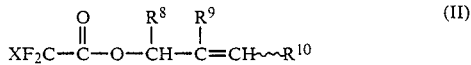

in which  signifies cis/trans isomers, X is Cl or Br, $R^8$ is H, $C_1$-$C_{24}$-alkyl or $C_6$-$C_{12}$-aryl, $C_7$-$C_{16}$-aralkyl or $C_8$-$C_{30}$-alkaralkyl which are unsubstituted or substituted in the aryl group by $C_1$-$C_6$-alkoxy, $C_1$-$C_6$-alkylthio, F, Cl, Br or —CN, $R^9$ and $R^{10}$ independently of one another are H or $C_1$-$C_{24}$-alkyl, $R^8$ and $R^9$ or $R^9$ and $R^{10}$ together are unsubstituted or $C_1$-$C_6$-alkyl-substituted $C_1$-$C_6$-alkylene or $C_3$-$C_6$-alkenylene, or $R^8$ and $R^{10}$ together are unsubstituted or $C_1$–$C_6$-alkyl-substituted $C_1$–$C_5$-alkylene or $C_2$–$C_5$-alkenylene.

The preferred definitions of $R^8$, $R^9$ and $R^{10}$ correspond to the preferred definitions of $R^1$, $R^2$ and $R^3$ respectively.

In a particular embodiment, $R^8$ is $C_1$–$C_{20}$-alkyl and $R^9$ and $R^{10}$ are H in the formula II.

A further preferred embodiment are compounds of the formula II, in which $R^8$ is H or $C_1$–$C_{20}$-alkyl and $R^9$ and $R_{10}$ are H or $C_1$–$C_6$-alkyl.

Another embodiment is represented by compounds of the formula II, in which $R^9$ is H and $R^8$ and $R^{10}$ together are unsubstituted or $C_1$–$C_6$-alkyl-substituted $C_1$–$C_6$-alkylene or $C_2$–$C_5$-alkenylene, or $R^{10}$ is H and $R^8$ and $R^9$ together are unsubstituted or $C_1$–$C_6$-alkyl-substituted $C_1$–$C_6$-alkylene or $C_3$–$C_6$-alkenylene, or $R^8$ is H and $R^9$ and $R^{10}$ are unsubstituted or $C_1$–$C_6$-alkyl-substituted $C_1$–$C_6$-alkylene or $C_3$–$C_6$-alkenylene.

The compounds of the formula II can be prepared in a manner known per se by esterification of bromo- or chlorodifluoroacetic acid with allyl alcohols of the formula III

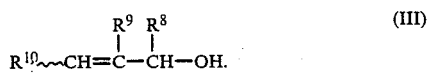

The allyl alcohols of the formula III are known or can be prepared in a known manner by reaction of aldehydes of the formula $R^8$—CH=O with vinylmagnesium bromides of the formula

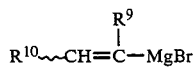

and subsequent hydrolysis.

Furthermore, the invention relates to compounds of the formula Ia

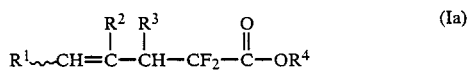

in which ⌇ signifies cis/trans isomers, $R^1$ is H, $C_1$–$C_{24}$-alkyl or $C_6$–$C_{12}$-aryl, $C_7$–$C_{16}$-aralkyl or $C_8$–$C_{40}$-alkaralkyl which are unsubstituted or substituted in the aryl group by $C_1$–$C_6$-alkoxy, $C_1$–$C_6$-alkylthio, F, Cl, Br or —CN, $R^2$ and $R^3$ independently of one another are H or $C_1$–$C_{24}$-alkyl, or $R^1$ and $R^3$ together are unsubstituted or $C_1$–$C_6$-alkyl-substituted $C_1$–$C_5$-alkylene or $C_2$–$C_5$-alkenylene, or $R^2$ and $R^3$ together or $R^1$ and $R^2$ together are unsubstituted or $C_1$–$C_6$-alkyl-substituted $C_1$–$C_6$-alkylene or $C_3$–$C_6$-alkenylene, and $R^4$ is —$SiR^5R^6R^7$, in which $R^5$ $R^6$ and $R^7$ independently of one another are $C_1$–$C_{12}$-alkyl, phenyl or benzyl, and to the acids and acid derivatives thereof, with the proviso that $R^1$, $R^2$ and $R^3$ cannot all be H at the same time.

The preferred definitions of $R^1$, $R^2$, $R^3$ and $R^4$ correspond to the preferred definitions of $R^1$, $R^2$, $R^3$ and $R^4$ in the compounds of the formula I.

In a preferred embodiment, $R^1$ in the formula Ia is $C_1$–$C_{20}$-alkyl and $R^2$ and $R^3$ are H.

Another preferred embodiment of compounds of the formula Ia are those in which $R^2$ is H and $R^1$ and $R^3$ together are unsubstituted or $C_1$–$C_6$-alkyl-substituted $C_1$–$C_6$-alkylene or $C_2$–$C_5$-alkylene, or $R^3$ is H and $R^1$ and $R^2$ together are unsubstituted or $C_1$–$C_6$-alkylsubstituted $C_1$–$C_6$-alkylene or $C_3$–$C_6$-alkenylene, or $R^1$ is H and $R^2$ and $R^3$ are unsubstituted or $C_1$–$C_6$-alkyl-substituted $C_1$–$C_6$-alkylene or $C_3$–$C_6$-alkenylene.

The compounds of the formulae I and Ia and their derivatives, especially the carboxylic acids, are suitable as monomers for the preparation of homopolymers or, together with monoolefinic or diolefinic monomers, for the preparation of copolymers. These polymers can be used as ion exchange resins. The polymers with carboxyl groups can be converted by means of transition metals or transition metal compounds into metal-organic polymers, the carboxyl groups of which have been partially or wholly reacted with the transition metals or transition metal compounds and which represent valuable catalysts (cf. German Offenlegungsschrift 2,605,247). Examples of suitable comonomers are olefins (ethylene, propylene, butylene, styrene, acrylic acid or methacrylic acid and their esters and amides, acrylonitrile and divinylbenzene).

The examples which follow illustrate the invention in more detail.

EXAMPLE 1

Allyl chlorodifluoroacetate

In a 1.5 liter sulfonation flask with a water separator, 294.0 g (2.25 mol) of chlorodifluoroacetic acid (pure, from Fluka AG) and 228.0 g (3.93 mol) of allyl alcohol are dissolved in 1 liter of chloroform and kept under reflux for 17 hours in the presence of 11.25 g of p-toluenesulfonic acid (0.06 mol), 41 ml of $H_2O$ separating out. The yellow reaction solution is washed twice with $H_2O$ and 3 times with saturated aqueous $NaHCO_3$ solution, dried over $MgSO_4$ and distilled under normal pressure through a Vigreux column. Yield: 306.0 g (80%) of a colourless oil of boiling point 98°–100° C./988 mbar.

EXAMPLES 2–8

Analogously to Example 1, further allyl chlorodifluoroacetates are prepared using substituted allyl alcohols. The relevant data are summarized in Table 1.

TABLE 1

| Example No. | $ClF_2C$—CO—R, R = | Boiling point [°C./mbar] | $^1H$—NMR ($CDCl_3$) δ(—O—$CH_n$—R) |
|---|---|---|---|
| 1 | $OCH_2CH=CH_2$ | 98–100/988 | 4.82 ppm, 2H |
| 2 | $OCH_2C(CH_3)=CH_2$ | 110/988 | 4.92 ppm, 2H |
| 3 | $OCH_2CH=CHCH_3$ | 52/32.5 | 4.78 ppm, 2H |
| 4 | $OCHCH=CH_2$ \| $(CH_2)_4CH_3$ | oil$^{(a)}$ | about 5.3 ppm, 1H |
| 5 | $OCH_2CH=CH(CH_2)_2CH_3$ | oil$^{(a)}$ | 4.80 ppm, 2H |
| 6 | $OCHCH=CHCH_3$ \| $CH_2CH_3$ | oil$^{(a)}$ | 5.26 ppm, 1H |
| 7 | $OCH_2CH=CHC_6H_5$ | oil$^{(a)}$ | 5.00 ppm, 2H |
| 8 | (cyclohexenyl-O) | oil$^{(a)}$ | 5.43 ppm, 1H |

$^{(a)}$Purification by chromatography on silica gel with $CH_2Cl_2$.

EXAMPLE 9

2,2-Difluoro-4-pentenoic acid 100.0 g (0.59 mol) of allyl chlorodifluoroacetate, 42.2 g (0.65 mol) of zinc dust (activated according to Fieser & Fieser), 96.7 g (0.88 mol) of trimethylchlorosilane and 400 ml of absolute acetonitrile are introduced together into a glass autoclave, a spatula tip of iodine is added and the mixture is heated for 48 hours at 100° C. The zinc salt which has precipitated is filtered off, the filtrate is hydrolysed with $H_2O$ and rendered basic with 2N NaOH. The dark brown aqueous phase, extracted with pentane, is acidified with half-concentrated HCl, and the product is extracted with ethyl acetate. After the organic phase has been dried over $MgSO_4$ and evaporated in a rotary evaporator (RE), the residue is distilled in vacuo. Yield: 59.4 g (74%) of a colourless oil of boiling point 73°–75° C./15.6 mbar.

EXAMPLES 10–15

Analogously to Example 9, the allyl chlorodifluoroacetates from Examples 2–6 and 8 are reacted. The relevant data are given in Table 2.

TABLE 2

| Example No. | Educt from Example No. | Product | $^1$H—NMR (CDCl$_3$) δ(—C$\underline{H}_n$—$\overset{\perp}{\text{CF}_2}$—COOR) |
|---|---|---|---|
| 9 | 1 | $CH_2$=$CHCH_2CF_2COOH$ | 2.87 ppm, 2H |
| 10 | 2 | $CH_2$=$C(CH_3)CH_2CF_2COOH$ | 2.83 ppm, 2H |
| 11 | 3 | $CH_2$=$CHCH(CH_3)CF_2COOH$ | 2.95 ppm, 1H |
| 12 | 4 | $CH_3(CH_2)_4CH$=$CHCH_2CF_2COOH$ | 2.81 ppm, 2H |
| 13 | 5 | $CH_2$=$CHCHCF_2COOH$<br>\|<br>$(CH_2)_2CH_3$ | 2.78 ppm, 1H |
| 14 | 6 | $CH_3CH_2CH$=$CHCH(CH_3)CF_2COOH$ | 2.91 ppm, 1H |
| 15 | 8 | (cyclohexenyl)—$CF_2COOH$ | 2.95 ppm, 1H |

EXAMPLE 16

Sodium 2,2-difluoro-4-pentenoate 4.01 g (29.9 mmol) of 2,2-difluoro-4-pentenoate acid are dissolved in 20 ml of methanol, and 1 equivalent of $NaOCH_3$ in methanol is added at room temperature (RT). After evaporation in the RE, 4.65 g (100%) of colourless crystals of melting point 168°–170° C. (decomposition) remain.

EXAMPLE 17

2,2-Difluoro-4-pentenoic acid chloride

In a round-bottomed flask with a distillation head, 57.2 g (0.42 mol) of 2,2-difluoro-4-pentenoic acid are slowly added dropwise to 102.0 g of phosphorus tetrachloride. After stirring for 20 minutes at RT, the reaction mixture is distilled, 42.1 g (65%) of the acid chloride passing over as a colourless oil at 92°–98° C./988 mbar. $^1$H-NMR (60 MHz, CDCl$_3$): 6.0–5.0 (m, 3H); 2.9 (d x t, J=6; 16 Hz, 2H).

EXAMPLE 18

Ethyl 2,2-Difluoro-4-pentenoate

Analogously to Example 1, 38.5 g (0.28 mol) of 2,2-difluoro-4-pentenoic acid are esterified with ethanol. Yield: 41.3 g (89%) of a colourless oil of boiling point 55°–57° C./52 mbar, $^1$H-NMR (60 MHz, CDCl$_3$): 6.1–5.0 (m, 3H); 4.30 (qa, J=7 Hz, 2H); 2.85 (d x t, J=16 Hz, 2H); 1.35 (t, J=7 Hz, 3H).

EXAMPLE 19

2,2-Difluoro-4-pentenoic acid amide

Aminolysis of 30.0 g (0.18 mol) of ethyl 2,2-difluoro-4-pentenoate (cf. Example 18) with 45 ml of 25% aqueous ammonia at RT gives, after extraction with ethyl acetate and distillation (130° C./26 mbar), 22.3 g (91%) of colourless crystalline amide. $^1$H-NMR (300 MHz, CDCl$_3$): 6.4 (broad, $NH_2$); 5.85–5.69 (m, 1H); 5.35–5.24 (m, 2H); 2.86 (m, 2H).

What is claimed is:

1. A process for the preparation of a compound of formula I $$R^1\text{---}CH=\overset{\overset{R^2}{|}}{C}\text{---}\overset{\overset{R^3}{|}}{CH}\text{---}CF_2\text{---}\overset{\overset{O}{\|}}{C}\text{---}OR^4 \quad (I)$$

in which ~~ signifies cis/trans isomers, $R^1$ is H, unsubstituted $C_1$–$C_{24}$-alkyl or $C_6$–$C_{12}$-aryl, $C_7$–$C_{16}$-aralkyl or $C_8$–$C_{40}$-alkaralkyl which are unsubstituted or substituted in the aryl group by $C_1$–$C_6$-alkoxy, $C_1$–$C_6$-alkylthio, F, Cl, Br or —CN, $R^2$ and $R^3$ independently of one another are H or $C_1$–$C_{24}$-alkyl, or $R^1$ and $R^3$ together are unsubstituted or $C_1$–$C_6$-alkyl-substituted $C_1$–$C_5$-alkylene or $C_2$–$C_5$-alkenylene, or $R^2$ and $R^3$ together or $R^1$ and $R^2$ together are unsubstituted or $C_1$–$C_6$-alkyl-substituted $C_1$–$C_6$-alkylene or $C_3$–$C_6$-alkenylene, and $R^4$ is $SiR^5R^6R^7$, in which $R^5$, $R^6$ and $R^7$ independently of one another are $C_1$–$C_{12}$-alkyl, phenyl or benzyl which comprises heating 1 mol of an allyl monobromo- or monochloro-difluoroacetate of the formula II $$XF_2C\text{---}\overset{\overset{O}{\|}}{C}\text{---}O\text{---}\overset{\overset{R^8}{|}}{CH}\text{---}\overset{\overset{R^9}{|}}{C}=CH\text{---}R^{10} \quad (II)$$

in which ~~ is as defined above, X is Cl or Br, $R^8$ is as defined for $R^1$, $R^9$ is as defined for $R^2$, $R^{10}$ is as defined for $R^3$, $R^8$ and $R^9$ are as defined for $R^1$ and $R^2$, $R^8$ and $R^{10}$ are as defined for $R^1$ and $R^3$, $R^9$ and $R^{10}$ are as defined for $R^2$ and $R^3$, in the presence of at least 1 mol of zinc and of at least 1 mol of a monochlorosilane $R^5R^6R^7SiCl$, in which $R^5$, $R^6$ and $R^7$ are as defined above and isolating the compound of formula I.

2. A process according to claim 1, wherein the formula I, $R^1$ is H, unsubstituted $C_1$–$C_{20}$-alkyl or phenyl, $C_7$–$C_{16}$-phenylalkyl or $C_8$–$C_{30}$-alkylphenylalkyl which are unsubstituted or substituted in the phenyl group by $C_1$–$C_6$-alkoxy, $C_1$–$C_6$-alkylthio, F, Cl, Br or —CN, $R^2$ and $R^3$ independently of one another are H or $C_1$–$C_{12}$-alkyl, or $R^1$ and $R^3$ together are $C_1$–$C_3$-alkylene or $C_2$–$C_3$-alkenylene, or $R^2$ and $R^3$ together or $R^1$ and $R^2$ together are $C_1$–$C_4$-alkylene, or $R^2$ and $R^3$ together or $R^1$ and $R^2$ together are $C_3$–$C_4$-alkenylene.

3. A process according to claim 1, wherein $R^1$ is H or $C_1$–$C_{20}$-alkyl and $R^2$ and $R^3$ are H or $C_1$–$C_6$-alkyl.

4. A process according to claim 1, wherein $R^5$, $R^6$ and $R^7$ are methyl.

5. A process according to claim 1, which is carried out at a temperature from 30° to 150° C.

6. A process according to claim 1, which is carried out in the presence of an inert, polar, aprotic solvent.

* * * * *